United States Patent [19]

Dixon

[11] Patent Number: 4,499,084

[45] Date of Patent: Feb. 12, 1985

[54] ARA-A ANTIVIRAL COMPOSITION AND METHOD OF ADMINISTERING THE SAME

[76] Inventor: Glen J. Dixon, P.O. Box 1328, Stone Mountain, Ga. 30086

[21] Appl. No.: 463,467

[22] Filed: Feb. 3, 1983

[51] Int. Cl.³ .................... A61K 31/70; C07H 19/16
[52] U.S. Cl. ..................................514/46; 536/24; 536/26
[58] Field of Search ...................... 536/24, 26; 424/180

[56] References Cited

U.S. PATENT DOCUMENTS

| | | | |
|---|---|---|---|
| 3,551,554 | 12/1970 | Herschler | 424/7 |
| 3,711,602 | 1/1973 | Herschler | 424/45 |
| 3,743,727 | 7/1973 | Herschler | 424/181 |
| 3,948,883 | 4/1976 | Ranganathan | 536/26 |
| 4,055,717 | 10/1977 | Baker et al. | 536/26 |
| 4,138,547 | 2/1979 | Christensen et al. | 536/26 |
| 4,199,574 | 4/1980 | Schaeffer | 424/200 |
| 4,338,310 | 7/1982 | Vince | 424/180 |

OTHER PUBLICATIONS

McGill, et al., "British Jour. of Ophthalmology", vol. 65, pp. 610-613, 1981.
Spruance, et al., "Annals of the New York Academy of Science", pp. 2-14, 1983.
MacCallum, et al., "British Medical Journal", vol. 2, pp. 805-807, 1966.
Hilton, et al., "British Jour. of Venereal Diseases", vol. 54, No. 1, pp. 50-52, 1978.
Goodman, et al., "Antimicrobial Agents and Chematherapy", vol. 8, No. 6, pp. 693-697, 1975.
Sloan, et al., "Antimicrobial Agents and Chemotherapy", pp. 161-171, 1969.
Klein et al., "Dimethyl Sulfoxide (DMSO) as a Vehicle for Antiviral Agents in Herpes Simplex Virus Skin Infections in Hairless Mice", *National Institute of Allergy and Infectious Diseases;* Presented at Contractors Meeting in Bethesda, Md., Mar. 27, 1979.
Klein et al., "Dimethyl Sulfoxide as a Vehicle for Antiviral Agents in Herpes Simplex Virus Skin Infections in Hairless Mice", *Current Chemother. Infec.,* Dig. 1980, pp. 1374-1376.
Dixon, et al., 1969, "Antiviral Activity of 9-B-D-Arabinofuranosyladenine, V. Activity Against Intracerebral Vaccina Virus Infections in Mice," *Antimicrobial Agents and Chemotherapy,* pp. 172-179.
Sidwell, et al., 1969, "Antiviral Activity of 9-B-D-Arabinofuranosyladenine, II., Activity Against Herpes Simplex Keratitis in Hamsters", *Antimicrobial Agents and Chemotherapy,* pp. 148-154.
Schardein, et al., 1969, "Antiviral Activity of 9-B-D-Arabinofuranosyladenine, III., Reduction in Evidence of Encephalitis in Treated Herpes Simplex--Infected Hamsters," *Antimicrobial Agents and Chemotherapy,* pp. 155-160.
Sloan, et al., 1969, "Antiviral Activity of 9-B-D-Arabinofuranosyladenine, IV., Activity Against Intracerebral Herpes Simplex Virus Infections in Mice," *Antimicrobial Agents and Chemotherapy,* pp. 161-171.
Hilton, et al., Feb. 1978, "A Trial of Adenine Arabinoside in Genital Herpes," *British Journal of Veneral Diseases,* pp. 50-52.
Goodman, et al., 1975, "Prospective Double-Blind Evaluation of Topical Adenine Arabinoside in Male Herpes Progenitalis," *Antimicrobial Agents and Chemotherapy,* vol. 8, No. 6, pp. 693-697.
MacCallum, et al., Oct. 1, 1966, "Herpes Simplex Virus Skin Infection in Man Treated with Idoxuridine in Dimethyl Sulphoxide, Results of Double-Blind Controlled Trial," *British Medical Journal,* pp. 805-807.
Turnbull, et al., Nov. 1969, "The Enhancing Effect of Dimethylsulfoxide Vehicle Upon the Anti-Viral Actions of 5-Iododeoxyuridine," *New Zealand Medical Journal,* pp. 317-320.
Juel-Jensen, et al., Dec. 1970, "Treatment of Zoster with Idoxuridine in Dimethyl Sulphoxide, Results of Two Double-Blind Controlled Trials," *British Medical Journal,* vol. 4, pp. 776-780.
Thormann, et al., 1980, "Contact Allergy to Idoxuridine, Sensitization Following Treatment of Herpes Zoster," *Contact Dermatitis,* vol. 6, pp. 170-171.
Burton, et al., Nov. 25, 1981, "On Trial, A Multicentre Trial of Zostrum (5 Percent Idoxuridine in Dimethylsulphoxide) in Herpes Zoster," *New Zealand Medical Journal,* pp. 384-386.
Silvestri, et al., Aug. 27, 1982, "Ineffectiveness of Topical Idoxuridine in Dimethyl Sulfoxide for Therapy for Genital Herpes," *JAMA,* vol. 248, No. 8, pp. 953-959.
Spruance, et al., 1983, "Dimethyl Sulfoxide as a Vehicle for Topical Antiviral Chemotherapy," *Annals of the New York Academy of Sciences,* pp. 1-14.
Babiuk, et al., Dec. 1975, "Comparison of the Antiviral Effects of 5-Methoxymethyldeoxyuridine with 5-Iododeoxyuridine, Cytosine Arabinoside, and Adenine Arabinoside," *Antimicrobial Agents and Chemotherapy,* vol. 8, No. 6, pp. 643-650.
Smith, et al., Feb. 1980, "In Vitro and In Vivo Resistance of Herpes Simplex Virus to 9-(2-Hydroxyethoxymethyl)quanine (Acycloguanosine)," *Antimicrobial Agents and Chemotherapy,* vol. 17, No. 2, pp. 144-150.
McGill, et al., 1981, "Comparative Trial of Acyclovir and Adenine Arabinoside in the Treatment of Herpes Simplex Corneal Ulcers," *British Journal of Opthalmology,* vol. 65, pp. 610-613.
DeClercq, et al., May 1980, "Comparative Efficacy of Antiherpes Drugs Against Different Strains of Herpes Simplex Virus," *The Journal of Infectious Diseases,* vol. 141, No. 5, pp. 563-573.
Davis, et al., Jun. 1981, "Genital Herpes Simplex Virus Infection: Clinical Course and Attempted Therapy," *Am. J. Hosp. Pharm.,* vol. 38, pp. 825-829.

*Primary Examiner*—Johnnie R. Brown
*Attorney, Agent, or Firm*—J. Rodgers Lundsford, III; Dale Lischer; William R. Cohrs

[57] ABSTRACT

There is disclosed an antiviral composition for treating herpes simplex virus disease and a method for administering the antiviral composition by topical application on the infected portion of the human body. The antiviral composition comprises a mixture of an antiviral agent, ara-A, and a solvent carrier medium, dimethyl sulfoxide.

11 Claims, No Drawings

ARA-A ANTIVIRAL COMPOSITION AND METHOD OF ADMINISTERING THE SAME

BACKGROUND OF THE INVENTION

This invention relates generally to antiviral agents, and more particularly concerns an antiviral agent, which when mixed with a solvent carrier agent, is effective to abate herpes simplex virus disease (commonly referred to as herpes) and other related viral diseases.

Herpes simplex virus disease as its name indicates is the result of the infection of the human body by the herpes simplex virus. The herpes simplex virus that affects humans is of two types, type 1 and type 2. Both types of herpes simplex virus infect the human body by penetrating the cellular wall of the body cells and interfering with the DNA configuration of the cells. The herpes simplex virus takes over the DNA mechanism of the cell so that the virus can replicate itself. In the process of the herpes virus replicating itself within the cell, the cell is destroyed. As a result of the destruction of body cells a blister-like sore appears at the location where the herpes virus entered the body.

The type 1 herpes simplex virus is generally acknowledged to produce the characteristic blister-like sores at the mucocutaneous junctions at the mouth, nose and eyes. The type 2 herpes simplex virus is generally acknowledged to create the same sort of blister-like sores on the genitals and anus. The sores can appear, however, at any location on the body such as a wound, where the virus can enter the body.

It is also commonly acknowledged that once the virus has entered the human body it never leaves. After the blister-like sores have healed in about two to three weeks, the herpes virus retreats to and lies dormant in the nerve tissue of the body. Herpes simplex virus from oral herpes sequesters in the trigeminial ganglion, and in genital herpes in the sacral ganglion. As a result, some people experience recurring blister-like sores which are thought to be brought on by stress or other unknown triggering mechanisms within the body. In other people, the virus may lie dormant for long periods of time or for the rest of the person's life.

For those people, however, that experience frequent recurring blister-like sores, especially those with genital herpes, the disease can be especially traumatic. While there are a number of antiviral agents which will destroy the herpes simplex virus in a laboratory setting, none of these antiviral agents have been successful in combating oral or genital herpes simplex virus disease in a clinical setting. These antiviral agents include adenine arabinoside (ara-A), ribavirin, acyclovir (ACV), 2-deoxy-d-glucose (DG) and phosphonacetic acid (PAA). R. Hamilton, *The Herpes Book*, pages 161-168, (J. P. Tarcher, Inc., 1980); F. E. Kahn, Ed., Vol. 27, *Antiobiotics and Chemotherapy*, (Harper, Basel, 1980); and W. M. Shannon and F. M. Sachael, Jr., Vol. II, *Pharmacology and Therapeutics*, pages 263-390, (Pergamon Press, Ltd., 1980).

At the present time, the Federal Food and Drug Administration (FDA) has approved the use of ara-A in ointment form for treatment of ocular herpes simplex virus disease. Moreover, ara-A has also been used in the treatment of herpes encephalitis by infusing a solution of ara-A in sterile infusion fluid for 12 to 24 hours. Neither of these treatments are effective against oral or genital herpes. "Vidarabine Ophalthalmic Ointment (Vira-A)", *Drug Therapy Bulletin*, May 25, 1979, 17(11), pages 43-44; and "Vidarbine Approval for Herpes Simplex Virus Encephalitis", *FDA Drug Bulletin*, Dec. 1978 Jan. 1979, 8(6) ¶ 36.

Also at the present time, the Burroughs Wellcome Company of Research Triangle Park, N.C., has offered for sale an ointment under the trademark Zovirax, the active antiviral agent of which is acyclovir. The acyclovir antiviral agent in the Zovirax ointment is mixed with a polyethylene glycol base. Burroughs Wellcome's own literature and advertising state that "in studies of recurrent herpes genitalis and herpes labialis in nonimmunocompromised patients, there was no evidence of clinical benefit . . ."

The antiviral agent IdU (5-iododexyuridine) has been combined with dimethyl sulfoxide (DMSO) and has purportedly cleared up skin lesions caused by DNA viruses, including herpes simplex and prevent recurrence. F. O. MacCallum and B. E. Juel-Jensen, *British Medical Journal*, 2 pages 805-807, (1966); B. C. Turnbull and H. C. W. Stringer, *New Zealand Medical Journal*, 70, pages 317-320, (1969); and B. E. Juel-Jensen, F. O. MacCallum, A. M. R. Mackenzie and M. C. Pike, *British Medical Journal*, 4 pages 776-780 (1970). P. McGrady, *The Persecuted Drug: The Story of DMSO*, page 285, Grosset & Dunlap Co., 1973 (1981).

The apparent problem in abating or curing herpes simplex virus disease in a clinical setting results from the difficulty of assuring that the antiviral agent penetrates the cellular wall into the infrastructure of the cell in order to attack and kill the herpes simplex virus that are literally hiding behind the cellular wall structure.

SUMMARY OF THE INVENTION

It is thus an object of the present invention to provide a composition of antiviral agent and a solvent carrier agent which, when combined, will translocate throughout the body and penetrate the cellular walls to attack the herpes simplex virus and destroy it.

It is a further object of the present invention to provide a composition of ara-A, an antiviral agent, and DMSO, a solvent carrier agent, which when mixed in proper proportions provides effective clinical abatement of herpes simplex virus disease resulting from both type 1 and type 2 herpes simplex viruses.

Other objects and advantages of the invention will become apparent upon reading the following detailed description of the invention.

DETAILED DESCRIPTION OF THE INVENTION

While the invention will be described in connection with a preferred embodiment, it will be understood that I do not intend to limit the invention to that embodiment. On the contrary, I intend to cover all alternatives, modifications and equivalents as may be included within the spirit and scope of the invention as defined by the appended claims.

As previously stated, ara-A (adenine-9-beta-D-arabinofuranoside) is known to be an effective antiviral agent against the herpes simplex virus. It is thought that ara-A does not work to combat herpes simplex virus disease in the clinical setting because ara-A is highly insoluble in water. As a result, the ara-A is not able to mix successfully with the body's fluids, and more importantly, it is not able to penetrate the cellular wall structure to get to the herpes simplex virus which is within the cell itself.

In order to assure that ara-A can be carried through the cell walls and into the cell structure, it is first necessary to dissolve ara-A in a suitable solvent system. Second, the solvent system media must have the ability to diffuse throughout the body and through the cell walls to carry the dissolved ara-A antiviral agent into the cell and into contact with the herpes simplex virus within the cell structure.

Thus the preferred embodiment of the present invention results from mixing the antiviral agent, ara-A, with DMSO (dimethyl sulfoxide), a solvent carrier agent.

Ara-A is active against a broad spectrum of DNA viruses (these are viruses which contain deoxyribonucleic acid as the predominant nucleic acid type) both in vitro (in the test tube) and in vivo (in animal models or in man). These viruses include the varicella-zoster virus (chicken pox and shingles), the Epstein-Barr (E-B) virus of infectious momonucleosis, vaccinia virus, cytomegalovirus and others.

The main reason ara-A is not active against oral and genital herpes is because of its low solubility in water (0.45 mg/ml at 25C). By using DMSO as the solvent system, it is possible to achieve a concentration of 10 mg/ml or greater. DMSO transports the ara-A directly into the virus infected cell where active viral replication is occurring. The drug interferes with viral DNA synthesis causing inhibition of viral maturation. Specifically, ara-A inhibits the enzyme DNA polymerase, an action that results in further viral replication.

Regarding toxicity or other side effects on the patient, extensive pharmacology and toxicity studies ara-A have been carried out in animals and in man. The acute intraperitoneal $LD_{50}$ for this drug ranged from 3900 to 4500 mg/kg in mice and 3300 to 2500 mg/kg in rats. This dose level indicates a low order of toxicity to a single parenteral dose. The acute oral $LD_{50}$ in both rats and mice is greater than 5000 mg/kg. This amount would be equivalent to more than 750 grams ($1\frac{2}{3}$ pounds) in an average 150 pound man. It is not possible to demonstrate toxicity through topical application of this compound. In some cases, however, redness and slight irritation has been noted after topical application. A massive acute overdosage of the intraveneous form of ara-A has been reported without any serious side effect. In the form used in the present invention and with treatment by topical application, it is highly unlikely that any toxic side effects of ara-A would be observed.

DMSO has been studied extensively also, in both animals and humans and is essentially nontoxic. When DMSO is applied to the skin in its undiluted state, it sometimes may cause an itching or burning sensation with redness or a rash. This rash, however, usually disappears shortly thereafter with no ill effects. *Annals of the New York Academy of Sciences*, Vol. 243, (1967). S. W. Jacob, E. E. Rosenhaum and D. C. Wood, Eds., Vol. 1 Dimethyl Sulfoxide 99, (marcel Depper, Inc., New York, N.Y. 1971); and *Annals of the New York Academy of Sciences*, Vol. 243 (1975). In the present invention DMSO is diluted to 70% with demineralized water before ara-A is added. At this concentration DMSO is usually nonirritating to normal skin.

DMSO serves two purposes in enhancing the therapeutic action of ara-A. First, DMSO allows a concentration of ara-A that is more than 20 times greater than can be achieved with water alone. Second, and more importantly, DMSO has the unique ability of permeating the interstitial spaces and cell walls to carry the antiviral drug along with it into the cell. It is this percutaneous property of DMSO that is apparently responsible for the extraordinary effectiveness of this medication.

Treatment of herpes simplex virus disease should begin as soon as prodromal symptoms are apparent. The prodrome or prodomal symptoms are the tingling, itching, burning sensations that occur a few hours to one to two days prior to manifestation of blisters or lesions. Usually if treatment is started at this early stage, the infection is aborted, and sores do not appear. When treatment is begun after lesions are present, the lesions resolve two to three days quicker than when left untreated. This shorter healing time means freedom from pain and virus shedding in a shorter time.

The medication should be applied every two to four hours for the first two days during waking hours. After that time, application every four to six hours is sufficient. If excessive irritation due to solvent is apparent, the time between applications should be increased to every six to eight hours, for example.

The antiviral composition of the present invention may be applied topically on the affected area with a cotton swab or gauze.

To say that a medication cures herpes would imply that the virus was not only inactivated and cleared from epithelial or mucousal cells, but that it was also cleared from the nerve cells where the virus lays dormant during latent periods. Because it is not known whether or not herpes virus replicates in the nerve cells, it is not known if the present invention inactivates the latent herpes virus in the nerve cells. It is entirely possible that the DMSO used in this medication does carry the antiviral drug into the nerve cell.

If ara-A does enter the nerve cell, and there is virus replication, then presumably the virus would be inhibited. Even if there is no virus replication occurring in the nerve cells, it is conceivable that the amount of virus in the body is decreased each time the virus becomes active and is attacked by treating in the prodrome. At some point after repeated treatment, the virus could become virtually nonexistent in the patient.

The formulation for the antiviral agent of the present invention is not critical and is effective over a wide range of concentrations of both ara-A and DMSO. A sample formula that has been used and is effective against both oral and genital herpes is as follows:

EXAMPLE 1

| | |
|---|---|
| Ara-A | 1.0 gm |
| DMSO | 70.0 ml |
| Demineralized Water | 30.0 ml |

The higher the concentration of DMSO is in the solvent carrier medium; the greater is the amount of ara-A that can be dissolved. Also, the therapeutic effectiveness of ara-A increases with concentration up to a point. The active concentration range with regard to DMSO is 50 to 100 percent of the solvent carrier medium. The ara-A range is 1.0 mg/ml to 100 mg/ml. An all encompassing formula, covering all useful concentration ranges by percentage is:

EXAMPLE 2

| | |
|---|---|
| Ara-A | 0.1 to 10.0 (of total composition) |

| | |
|---|---|
| DMSO | 50 to 100 (of solvent carrier medium) |
| Demineralized water | 0 to 50 (of solvent carrier medium) |

Another ingredient or component that might be usefully added to the composition is a local anesthetic such as benzocaine or dibucaine which may be incorporated into the medication for local pain control. The medication of the present invention has been prepared and used both ways. It appears that the presence of benzocaine does not impair the antiviral activity of ara-A. Nor does the benzocaine appear to have any deleterious affect on the patient when administered in DMSO. Also 1-2 percent carboxymethylcellulose might be added to the mixture to provide a gel which may be preferred for topical application for vaginal and cervical herpes.

There are no special procedures involved in the preparation of the antiviral composition of the present invention. The demineralized water and DMSO can be mixed and the ara-A (and benzocaine if used) dissolved in the DMSO and water solution. The ara-A can be added to the pure DMSO, and water added last. When water and DMSO are mixed, the solution becomes warm because there is a positive heat of solution. There is no chemical reaction between ara-A and DMSO under the conditions of preparation. Ara-A can be recovered from the DMSO and water solution virtually 100 percent as unchanged ara-A.

In addition to the preferred embodiment described using ara-A as the antiviral agent, the present invention also encompasses those analogs of ara-A which display significant antiviral activity by interferring viral DNA synthesis to inhibit viral maturation. Thus, for example, acyclovir and ribavirin, which are similar to ara-A in that all three are purine analogs, will, when mixed with DMSO, provide clinical benefits against oral and genital herpes. Of course, other analogs of ara-A may be expected to provide similar benefits when mixed with DMSO.

I claim:

1. An antiviral composition for treating herpes simplex virus disease in humans comprising a solvent carrier which will translocate throughout the body and penetrate cell walls and an antiviral agent which interferes with viral deoxynucleic acid synthesis causing inhibition of viral maturation wherein the solvent carrier includes dimethyl sulfoxide and water and wherein the antiviral agent is ara-A.

2. A method for treating herpes simplex virus disease in humans comprising the step of topically applying every two to four hours to infected portions of the human body an antiviral composition comprising a solvent carrier which will translocate throughout the body and penetrate cell walls and an antiviral agent which interferes with viral deoxynucleic acid synthesis causing inhibition of viral maturation, wherein the solvent carrier includes dimethyl sulfoxide and wherein the antiviral agent is ara-A.

3. The method for treating herpes simplex virus disease in humans of claim 2, wherein the antiviral composition further comprises a local anesthetic.

4. The method for treating herpes simplex virus disease in humans of claim 2, wherein the antiviral composition further comprises a gel forming agent.

5. An antiviral composition for treating herpes simplex virus disease in humans comprising a solvent carrier which will translocate throughout the body and penetrate cell walls and an antiviral agent which interferes with viral deoxynucleic acid synthesis causing inhibition of viral maturation, wherein the solvent carrier includes dimethyl sulfoxide and water and wherein the antiviral agent is purine analog of ara-A and is selected from the group consisting of acyclovir and ribavirin.

6. A method for treating herpes simplex virus disease in humans comprising the step of topically applying every two to four hours to infected portions of the human body an antiviral composition comprising a solvent carrier which will translocate throughout the body and penetrate cell walls and an antiviral agent which interferes with viral deoxynucleic acid synthesis causing inhibition of viral maturation, wherein the solvent carrier includes dimethyl sulfoxide and wherein the antiviral agent is a purine analog of ara-A and is selected from the group consisting of acyclovir and ribavirin.

7. The antiviral composition of claim 1, having the following proportions by percentage weight: ara-A is 0.1 to 10.0 percent of the total composition, dimethyl sulfoxide is 50 percent to less than 100 percent of the solvent carrier, and demineralized water is greater than 0 percent up to 50 percent of the solvent carrier.

8. The antiviral composition of claim 1, having the following approximate proportions: 1.0 gram of ara-A, 70.0 milliliters dimethyl sulfoxide, and 30.0 milliliters demineralized water.

9. The method for treating herpes simplex virus disease in humans of claim 2, wherein solvent carrier further includes water.

10. The method for treating herpes simplex virus disease in humans of claims 2 or 9, having the following proportions by percentage weight: ara-A is 0.1 to 10.0 percent of the total composition, dimethyl sulfoxide is 50 to 100 percent of the solvent carrier, and demineralized water is 0 to 50 percent of the solvent carrier.

11. The method for treating herpes simplex virus disease in humans of claim 9, wherein the antiviral composition comprises the following approximate proportions: 1.0 gram of ara-A, 70.0 milliliters dimethyl sulfoxide, and 30.0 milliliters demineralized water.

* * * * *